Feb. 25, 1941. W. E. LAMMERTS Plant Pat. 456
ROSE PLANT
Filed Oct. 14, 1940
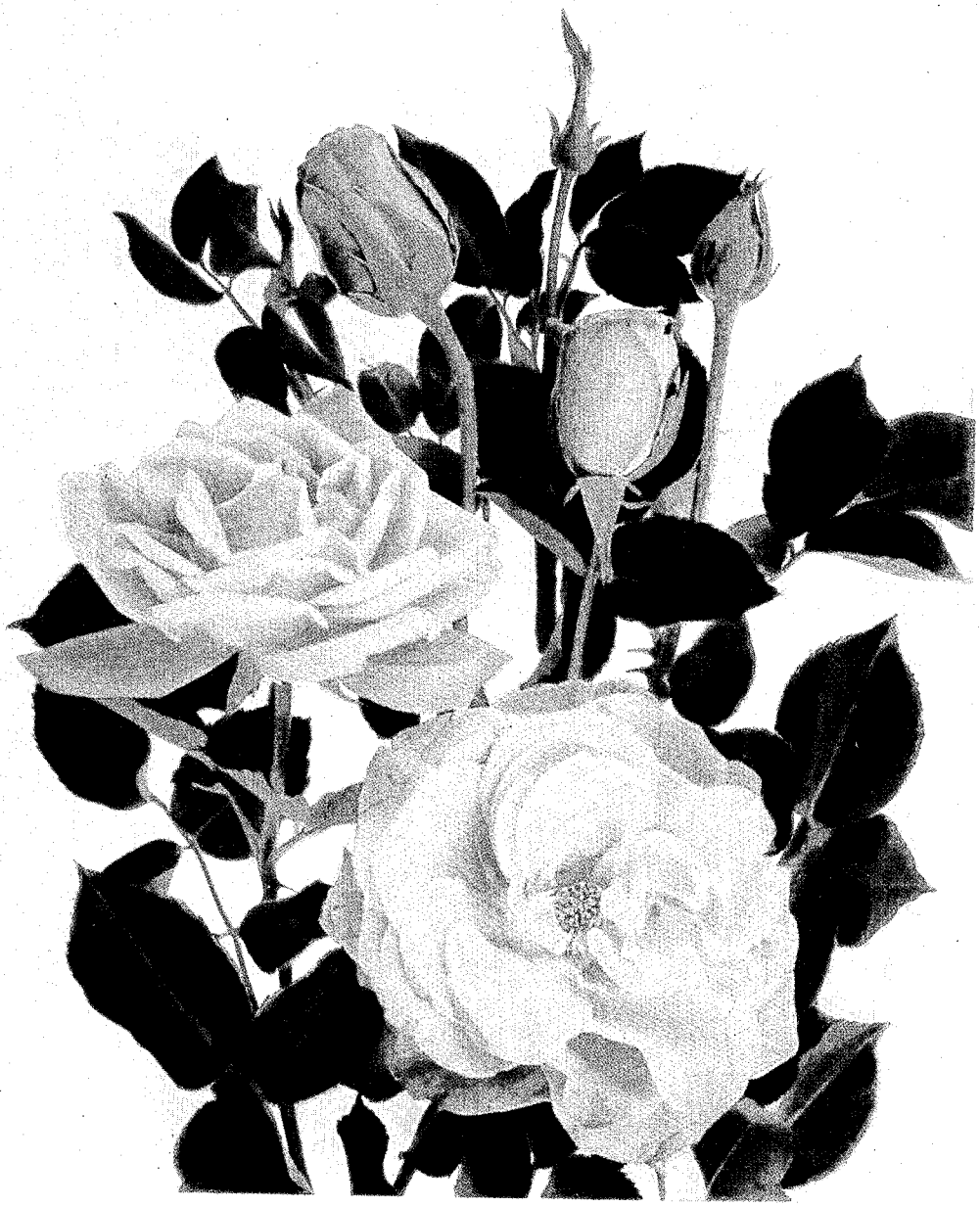
Inventor
W. E. Lammerts
By Robert Robb
attorneys Patented Feb. 25, 1941

Plant Pat. 456

UNITED STATES PATENT OFFICE

456

ROSE PLANT

Walter E. Lammerts, Ontario, Calif., assignor to Armstrong Nurseries, Ontario, Calif., a corporation of California Application October 14, 1940, Serial No. 361,192

1 Claim. (Cl. 47—61)

This invention relates to a new and distinct variety of rose plant, originating as a seedling resulting from a cross of two well known varieties "Charles P. Kilham" and "President Hoover."

The new rose combines a number of the desirable characteristics of its parents, receiving apparently its habit of vigorous growth and tendency to long foliaceous sepals from President Hoover, and its spreading manner of growth of clasping type of sepals from its other parent. The flowers incorporate the colors of both parents, giving rise to an extraordinary color arrangement of particular value for cut flowers as well as garden decoration.

More specifically, the novel and distinguishing features of the new variety which I believe are of primary importance are as follows:

The vigorous, somewhat spreading habit of growth; the thick, leathery leaves which are of large size where the plants are well grown; the unusually long, heavy stems supporting the flower on a stiff peduncle of rather large size and unusual length; the more than normal tendency to produce only one flower per stem; the extremely long, urn-shaped buds, Spectrum Red in cool weather to Rose Doree in hot weather, opening to huge flowers, four to six inches across, varying in color when open from Carmine to Spectrum Red to Begonia Rose, with a center of Lemon Chrome.

The tea fragrance of the flower is quite pronounced, as is the thick heavy substance of the petals which are extremely large on the outer portion of the flower. The foliage is extremely mildew-resistant here in southern California.

The following is a detailed description of this new rose, the color terminology employed therein being in accord with Ridgway's Color Standard.

Type: Tender; tall; bush; outdoor; seedling; for cut flowers and garden decoration.

Class: Hybrid tea.

Parentage:

*Seed Parent.*—Charles P. Kilham.

*Pollen Parent.*—President Hoover.

Propagation: Holds its distinguishing characteristics through succeeding propagations by budding.

*Flower*

Locality where grown: Ontario, California.

Flowers borne: Usually singly, occasionally two, three, four, five or several to stem; in irregular cluster; on strong long stems.

Quantity of bloom: Free; outdoors.

Continuity: Continuous during rose season.

Fragrance: Strong; tea.

Bud:

*Peduncle.*—Long; heavy; erect; stiff; almost smooth; few gland-tipped cilia and small prickles. *Color*—Chromium Green, Plate XXXII, to Deep Malachite Green, Plate XXXII, at tip; flushed on sunny side with Light Vinaceous Purple, Plate XLIV, to Vinaceous Purple, Plate XLIV.

*Before calyx breaks.*—*Size*—large. *Form*—ovoid; with foliaceous appendages on the surface of the bud; with slender much cut foliaceous parts extending beyond the tip of the bud equal to three-fourths or more of its length.

*As calyx breaks.*—*Color*—between Carmine, Plate I, and Spectrum Red, Plate I. Inner surface with fine, woolly tomentum; margins exposed before calyx breaks lined with gland-tipped cilia and foliaceous appendages. Margins not exposed before calyx breaks lined with fine tomentum.

*As first petal opens.*—*Size*—large. *Form*—very long, pointed to urn-shaped. *Color:* outside—Spectrum Red, Plate I, to Rose Doree, Plate I; small area at base near Light Greenish Yellow, Plate V; Inside—Rose Color, Plate XII, to Rose Red, Plate XII, tips early becoming Phlox Pink, Plate XI, to Rosolane Pink, Plate XXVI; slightly larger area at base than outside between Lemon Chrome, Plate IV, and Strontian Yellow, Plate XVI. Opening—opens up well. It is easily damaged by thrips, and outside petals are frequently so damaged when thrips are prevalent.

Bloom:

*Size, when fully open.*—Very large, four inches to six inches.

*Petalage.*—Semi-double to double (more petals, but the stamens not hidden); from 30 to 40 petals arranged irregularly in center.

*Form.*—High center at first, becoming open to flat; petals at first tightly rolled outward; becoming later, at maturity, very loosely rolled outward.

Petals: Thick; leathery; with inside and outside satiny.

*Shape.*—Outside—broadly ovate; scalloped with one, two or three notches. Intermediate — broadly ovate-cuspidate, usually entire. Inside — ovate-cuspidate, usually entire.

*Color.*—Colors may be modified by being tinted with Carmine, Plate I, to Spectrum Red, Plate I, on outside of bud color changing at tip as bud opens to near Light Mallow Purple, Plate XII.

This description of a newly opened flower was made from a rose grown outdoors in August, 1940, at Ontario, California:

*Color.*—Outside petal: outside surface—Rose Doree, Plate I, to Spectrum Red, Plate I; small area of Light Greenish Yellow, Plate V, at base; inside surface—Rose Doree, Plate I; small area of Lemon Chrome, Plate IV, at base. Tips Begonia Rose, Plate I. Intermediate petal: outside surface—Rose Doree, Plate I, small area Light Greenish Yellow, Plate V, at base; inside surface—Rose Doree, Plate I, area of Lemon Chrome, Plate IV, at base. Inner petal: outside surface—near Deep Rose Pink, Plate XII, to near Light Greenish Yellow, Plate V, at base; inside surface—near Rose Color, Plate XII, to near Light Greenish Yellow, Plate V, at base.

This description was made from a rose that was cut outdoors and open for three days indoors, in August, 1940, at Ontario, California:

*Color.*—Outside petal: outside surface—General color effect of near Amparo Purple, Plate XI, to Pale Amaranth Pink, Plate XII, to near Light Viridine Yellow, Plate V, at base; inside surface—Phlox Pink, Plate XI, with markings of Phlox Purple, Plate XI, on veins; near Pale Greenish Yellow, Plate V, at base; inside petal: outside surface—near Rose Pink, Plate XII, midrib near Sulphur Yellow, Plate V, with base near Light Viridine Yellow, Plate V; inside surface—between Amaranth Pink, Plate XII, and Deep Rose Pink, Plate XII, with Lemon Chrome, Plate IV, at base.

*General color effect.*—Newly opened flower—Rose Red, Plate XII, to Spectrum Red, Plate I, varying to Rose Doree, Plate I; three days open—Eosine Pink, Plate I, to near Deep Rose Pink, Plate XII.

*Behavior.*—Persist. Is not affected by cold, hot, wet, dry weather except in color variations fading from near Light Greenish Yellow, Plate V, at base through Mallow Pink, Plate XII, Light Mallow Purple, Plate XII, to near Ochraceous Tawny, Plate XV, at tip as petals wither.

*Flower longevity.*—On bush in garden four days in August; cut roses grown outdoors kept at living room temperatures four days in August.

*Reproductive organs*

Stamens: Medium many, arranged irregularly, partly, about pistils, mixed with petaloids slightly.

Filaments: Medium to long; most with anthers; color varying from Begonia Rose, Plate I, to near Deep Chrome, Plate III.

Anthers: Large; open at various times; color near Apricot Yellow, Plate IV.

Pollen: Moderate; near Cadmium Yellow, Plate III.

Pistils: Many.

Styles: Uneven; medium to long; thin; loosely bunched; Carmine, Plate I, near stigma to near Maize Yellow, Plate IV, at base.

Stigma: Near Ochraceous Buff, Plate XV.

Ovaries: All enclosed in calyx.

Hips: Rarely set hips.

Sepals: Permanent; long; spear-shaped and curled slightly.

*Color.*—Inside—near Corydalis Green, Plate XLI, to Greenish Glaucous, Plate XLI; outside—Deep Turtle Green, Plate XXXII, at base to near Deep Dull Yellow Green, Plate XXXII, (1) at tip.

*Plant*

Foliage:

*Leaves.*—Compound of three to seven leaflets; moderately abundant; large; very heavy leathery.

*Leaflets.*—Ovate to ovate-cuspidate, with apex acute to mucronate; base round; margin simply serrate.

*Color.*—*Mature:* upper surface—near Dusky Green, Plate XXXIII; under surface, near Civette Green, Plate XVIII. *Young:* upper surface—near Bordeaux, Plate XII, at edges, near Yellowish Olive, Plate XXX, in middle; under surface, near Dahlia Carmine, Plate XXVII.

*Rachis.*—Medium heavy. Upper side—grooved, hairy, glandular. Under side—sparsely prickly; prickles small $\frac{1}{16}''$ slightly hooked.

*Stipules.*—Moderately long; narrow, with medium long points usually turning out at an angle of more than 45°, sometimes recurved toward the stem.

*Disease.*—Resistant to mildew.

Growth:

*Habit.*—Bushy; upright to spreading; much branched.

*Growth.*—Free to vigorous.

*Canes.*—Moderately heavy.

*Main stems.*—Near Calla Green, Plate V, with cracks in bark forming corky linear dots and lines of near Cinnamon, Plate XXIX, to Pecan Brown, Plate XXVIII, and shading of near Anthracene Purple, Plate XLIV, to Victoria Lake, Plate I, on sides exposed to sun. *Large prickles*—several; medium to long; hooked downward slightly, with short broad base; near Russet, Plate XV, in color. *Small prickles*—few; near Russet, Plate XV, in color.

*Branches.*—Color near Rinnemann's Green, Plate XVIII. *Large prickles*—several; medium to long, hooked downward slightly with short broad base: Color near Honey Yellow, Plate XXX, at base to near Ochraceous Buff, Plate XV, toward tip. *Small prickles*—few; color near Honey Yellow, Plate XXX, at the base to near Ochraceous Buff, Plate XV, toward tip. *Hairs*—none.

*New shoots.*—Near Dark Livid Brown, Plate XXXIX, where exposed to sun and near Cosse Green, Plate V, where unexposed. *Large prickles*—several; medium to long; straight to hooked downward slightly; with short broad base; near Pansy Purple, Plate XII, at base to near Grape Green, Plate XLI, at tip. *Small prickles*—none to few; near Pansy Purple, Plate XII, at base to near Grape Green, Plate XLI, at tip. *Hairs*—none.

I claim:

A new and distinct variety of hybrid tea rose plant, characterized as to novelty by its vigorous spreading habit of growth; size and texture of its foliage; long, heavy stems; resistance to mildew; tendency to produce only one flower per stem; particular shape and color of the bud; large size and unusual coloring of the open flower; the texture of the petals, and the pronounced fragrance of the flower, substantially as shown and described.

WALTER E. LAMMERTS.